(12) United States Patent
Hakes

(10) Patent No.: US 7,387,086 B2
(45) Date of Patent: *Jun. 17, 2008

(54) BOVINE GERMICIDE APPLICATION DEVICE AND METHOD

(76) Inventor: Dennis Lee Hakes, 943 Wanda La., Heyburn, ID (US) 83336

(*) Notice: Subject to any disclaimer, the term of this patent is extended or adjusted under 35 U.S.C. 154(b) by 0 days.

This patent is subject to a terminal disclaimer.

(21) Appl. No.: 11/303,550

(22) Filed: Dec. 15, 2005

(65) Prior Publication Data

US 2006/0102095 A1 May 18, 2006

Related U.S. Application Data

(62) Division of application No. 10/913,265, filed on Aug. 6, 2004, now Pat. No. 7,165,510.

(60) Provisional application No. 60/517,299, filed on Nov. 4, 2003.

(51) Int. Cl.
*A01K 29/00* (2006.01)

(52) U.S. Cl. .............. 119/652; 119/14.02; 119/650; 604/310

(58) Field of Classification Search .......... 119/650–678, 119/602–606; 604/310
See application file for complete search history.

(56) References Cited

U.S. PATENT DOCUMENTS

| | | | | |
|---|---|---|---|---|
| 2,952,860 A | * | 9/1960 | George ......................... 15/29 |
| 3,267,903 A | * | 8/1966 | Valentine ..................... 119/664 |
| 3,366,111 A | * | 1/1968 | Gandier ....................... 604/310 |
| 3,648,696 A | * | 3/1972 | Keith ........................... 604/310 |
| 3,713,423 A | * | 1/1973 | Sparr, Sr. ..................... 119/670 |
| 4,305,346 A | * | 12/1981 | Sparr, Sr. ..................... 119/670 |
| 4,619,009 A | * | 10/1986 | Rosenstatter ................... 15/29 |
| 4,903,639 A | * | 2/1990 | Kessel ......................... 119/651 |
| 5,235,937 A | * | 8/1993 | Farina et al. .................. 119/664 |
| 5,535,700 A | * | 7/1996 | Boudreau ...................... 119/651 |
| 5,673,650 A | * | 10/1997 | Mottram et al. ............... 119/651 |
| 6,269,512 B1 | * | 8/2001 | Thomson et al. ............ 15/104.92 |
| 6,302,058 B1 | * | 10/2001 | Dahl et al. ................... 119/14.47 |

(Continued)

FOREIGN PATENT DOCUMENTS

EP 0029240 5/1981

(Continued)

OTHER PUBLICATIONS

International Preliminary Report on Patentability, PCT/US2004/036873.

*Primary Examiner*—Teri Pham Luu
*Assistant Examiner*—Joshua J Michener
(74) *Attorney, Agent, or Firm*—Stephen M. Nipper; Derek H. Maughan; Dykas, Shaver & Nipper, LLP

(57) ABSTRACT

A method and device for applying germicide solutions to a cattle teat or other item in a way that reduces the amount of waste that typically accompanies this process. The present invention provides a method for cleaning a teat which comprises the steps of dipping a teat into a quantity of a preselected germicidal solution so as to coat that teat, wiping excess material from that teat and collecting the removed excess material from the teat. The present invention also provides an improved germicide applicator for use in the invented method.

1 Claim, 4 Drawing Sheets

U.S. PATENT DOCUMENTS

| | | | | |
|---|---|---|---|---|
| 6,318,299 B1 * | 11/2001 | Birk | ............................ | 119/651 |
| 6,321,682 B1 * | 11/2001 | Eriksson et al. | ........... | 119/14.44 |
| 6,321,688 B1 * | 11/2001 | Eriksson | ...................... | 119/663 |
| 6,325,021 B1 * | 12/2001 | Farina | ......................... | 119/664 |
| 6,394,038 B1 * | 5/2002 | Eriksson | ..................... | 119/609 |
| 6,626,130 B1 * | 9/2003 | Eriksson | ..................... | 119/670 |
| 6,752,102 B2 * | 6/2004 | Dahl et al. | ................ | 119/14.47 |
| 6,935,271 B2 * | 8/2005 | Edison et al. | ............. | 119/14.47 |
| 2002/0096541 A1 * | 7/2002 | Cross | .......................... | 222/190 |

FOREIGN PATENT DOCUMENTS

| | | |
|---|---|---|
| EP | 0399132 | 11/1990 |
| GB | 2376888 | 12/2002 |
| JP | 2002078427 | 3/2002 |

* cited by examiner

BOVINE GERMICIDE APPLICATION DEVICE AND METHOD

PRIORITY

This application is a divisional application of and claims priority from a previously filed utility patent application entitled BOVINE GERMICIDE APPLICATION DEVICE with application Ser. No. 10/913,265 filed by the same inventor on Aug. 6, 2004, now U.S. Pat No. 7,165,510 which in turn claimed priority from an earlier filed provisional application entitled TEAT DIPPER filed by Dennis Lee Hakes on Nov. 4, 2003 with application Ser. No. 60/517,299, the contents of which are herein incorporated by reference.

BACKGROUND OF THE INVENTION

1. Field of the Invention

The present invention generally relates to veterinary and animal care equipment and more particularly to devices that are utilized to support and maintain proper care of udders and teats in lactating animals.

2. Background Information

For the health and safety of milk producing animals as well as those persons and animals that consume the milk products derived from these animals, the udders and teats of milk producing animals must be kept clean and healthy. This is particularly true in the bovine dairying industry where complications such as mastitis, swollen or cracked teats, and dirty and unclean teats can cause bacterial contamination of entire vats of milk. This contamination can render hundreds or even thousands of gallons of milk useless and can have severe economic effect on the dairyman who depends upon the sale of acceptable uncontaminated milk as a source of income. The economic impacts of contaminated or unacceptable milk can be devastating.

In order to prevent mastitis and other complications and to maintain a healthy milk supply, the care, cleaning and hygiene of the teats and udders of the animals being milked is of particular importance. In order to prevent the onset of mastitis, a variety of procedures are utilized to stimulate, clean and disinfect the teats of the animal. Most mastitis infections are related to conditions that expose the teat end to bacteria and to situations that make it easier for these bacteria to penetrate the teat canal. These bacteria then travel into the mammary gland where the infection causes an inflammatory response that can cause destruction of milk secreting cells as well as contaminating any of the milk that comes from these infected cows.

While various precautions have been taken to prevent the cow from developing mastitis, such as pre-washing, stripping, and sanitizing of the milking equipment, the most effective way of preventing the onset of mastitis involves the use of so called teat-dip to apply a germicide to the teat both prior to and after milking. The application of teat dip prior to milking typically requires that a teat be dipped into a cup having a germicidal solution. The teat is then coated and after about 30 seconds the germicide is dried off of the teat with a paper or cloth towel. This germicide destroys those microorganisms that contaminate the teat skin between milkings. After milking has been completed, the teats are again dipped into these cups and coated with a germicide. This germicide prevents the growth and proliferation of organisms that can cause mastitis.

The application of teat dip to the teat is of utmost importance. It is crucial that the entire teat be completely covered and that a residue is left on the teat so that the anti-microbial action is still present when the cow lies down in a free stall or any other place where sanitary conditions are less than ideal. Barrier teat dips generally contain germicides, skin conditioners and protective film so that the teat end is sealed from mastitis-causing bacteria. These barrier teat dips do inhibit bacterial multiplication on the teat skin under the film.

One of the known methods and devices for applying teat dip is to utilize a dip cup of a sprayer to coat the teat. The teat is typically dipped into the cup or sprayed so as to apply the germicide. This presents several problems. First, obtaining the proper coverage over the teat is not always accomplished, as the location of the germicide upon the teat is dependent upon the skill of the person applying the solution to the teat. Thus, locations or areas of the teat may not be covered and may be left exposed. These uncovered areas provide locations wherein bacteria can congregate and proliferate. When this occurs, the effectiveness of the teat dip as a whole has been compromised.

Both the dip and the spray method that exist in the prior art cause substantial amounts of waste to take place. This waste occurs as excess material does not adhere to the teat, falls off of the teat and on to the floor where it is subsequently washed away. This germicide is a highly corrosive material that can then cause various economic and environmental damage to the areas in which it contacts. This problem is exacerbated by the spreading of the wasted solution, which is then washed into ponds of manure pits, and then spread upon the ground. These germicides are hazardous to clean water and the raising of crops on the earth.

The economic impact of this waste is also great. The dairy industry has become extremely economically conservative because of low prices received for their product. Therefore, the ability to reduce waste is of great value. A gallon of post dip for example, varies in price from between $5 and $15 dollars per gallon. A typical 1,000-head milking herd may require an average of about 350 gallons per month. Thus, the cost of utilizing this dip may be between about $1,750 and $5,250 per month. The ability to reduce this cost would greatly benefit a user and could provide, in some instances, the difference between a farm surviving or failing.

Accordingly, what it needed is a way to apply germicidal solutions to animal teats, which results in less runoff, less waste, and increased economic savings to the user. What is also needed is a way to reduce the amount of germicidal solution that is consumed by a dairy operation without compromising the benefits of dipping or treating teats with a germicidal solution. What is also needed is a device that would assist a user in performing this teat dipping procedure in a way that would reduce the amount of wasted solution while providing adequate coverage over the teat itself. Accordingly, it is an object of the present invention to provide a method and device for providing improved efficacy in the application of germicidal teat dip to animals and which significantly reduces the quantity of material that is consumed and wasted in such a process. It is a further object of the invention to provide a method for dipping cattle teats that produces less waste, and obtains better coverage of the teat than those methods that exist in the prior art. It is a further object of the invention to provide a device that allows a user to apply a germicidal solution to a teat that ensures proper and adequate coverage over this teat and that captures excess material so as to prevent the waste of this excess material.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention is a method and device for applying germicide solutions to a cattle teat or other item in a way that reduces the amount of waste that typically accompanies this process. The present invention provides a method for cleaning a teat, which comprises the steps of dipping a teat into a quantity of a preselected germicidal solution so as to coat that teat, wiping excess material from that teat and collecting the removed excess material from the teat. The present invention also provides an improved germicide applicator for use in the invented method.

The device of the present invention is made up of a cleansing application device. This cleansing application device has a chamber with an open first end and a generally closed second end. A wiping device is also positioned near the open first end. This open first end and the wiping device are configured to receive a teat therein. The chamber is configured to hold a quantity of teat dip germicidal solution therein. In use, the invention is pushed up around the teat of a cow until the desired portion of the teat is covered. The teat is then coated with the germicidal solution. The device is then moved downward and the excess teat dip solution is wiped off of the teat and is recollected within the chamber. This device provides a substantial benefit because it reduces the amount of germicidal solution that is wasted.

In the preferred embodiment, the cleansing device is attached to a reservoir container made of a compressible material, and a transport conduit extends from within this reservoir container to a circumvolving ring positioned near the wiping device at the top portion of the cleaning container. When the reservoir container is squeezed, germicide from the reservoir is pushed up through the transport conduit and wets the wiping device, which in the preferred embodiment is a generally circular shaped brush. This germicide solution then wets the bristles and provides an application device for ensuring that the entire teat is covered, both from being dipped as well as from being wiped by the wiping device. When the teat is removed from within the container, the wiping device wipes the teat and the cleansing chamber recollects all of the excess material that would otherwise drip and fall from the teat.

The present invention provides a teat cup with a barrier and wiping mechanism, which ensures proper coverage of the teat with germicidal solution while also limiting the amount of germicidal applicant, which is wasted. The germicidal solution is applied through the barrier device and also allows the end of the teat to be placed within a teat cup chamber. When the teat is removed from the teat cup, the wiping mechanism wipes the teat and ensures that the appropriate quantity of disinfectant is located and positioned upon the device. The excess material is then pushed back into the teat dip cup and is conserved for future use. This concentrates the liquid that is utilized to that amount that is placed upon the teat and significantly reduces the amount that falls to the ground or that is otherwise wasted with the prior art devices.

The present invention provides significant cost savings to a user. For example, the applicator of the present invention would reduce the amount of post dip from about 350 gallons per month to about 90 gallons per month. This would result in a cost savings of between $1,300 and $3,900 per month depending upon the type of dip that is used. The present invention also increases the coverage of the teat as compared to other devices The purpose of the foregoing Abstract is to enable the United States Patent and Trademark Office and the public generally, and especially the scientists, engineers, and practitioners in the art who are not familiar with patent or legal terms or phraseology, to determine quickly from a cursory inspection, the nature and essence of the technical disclosure of the application. The Abstract is neither intended to define the invention of the application, which is measured by the claims, nor is it intended to be limiting as to the scope of the invention in any way.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive in nature.

DESCRIPTION OF THE PREFERRED EMBODIMENTS

Figure 1:
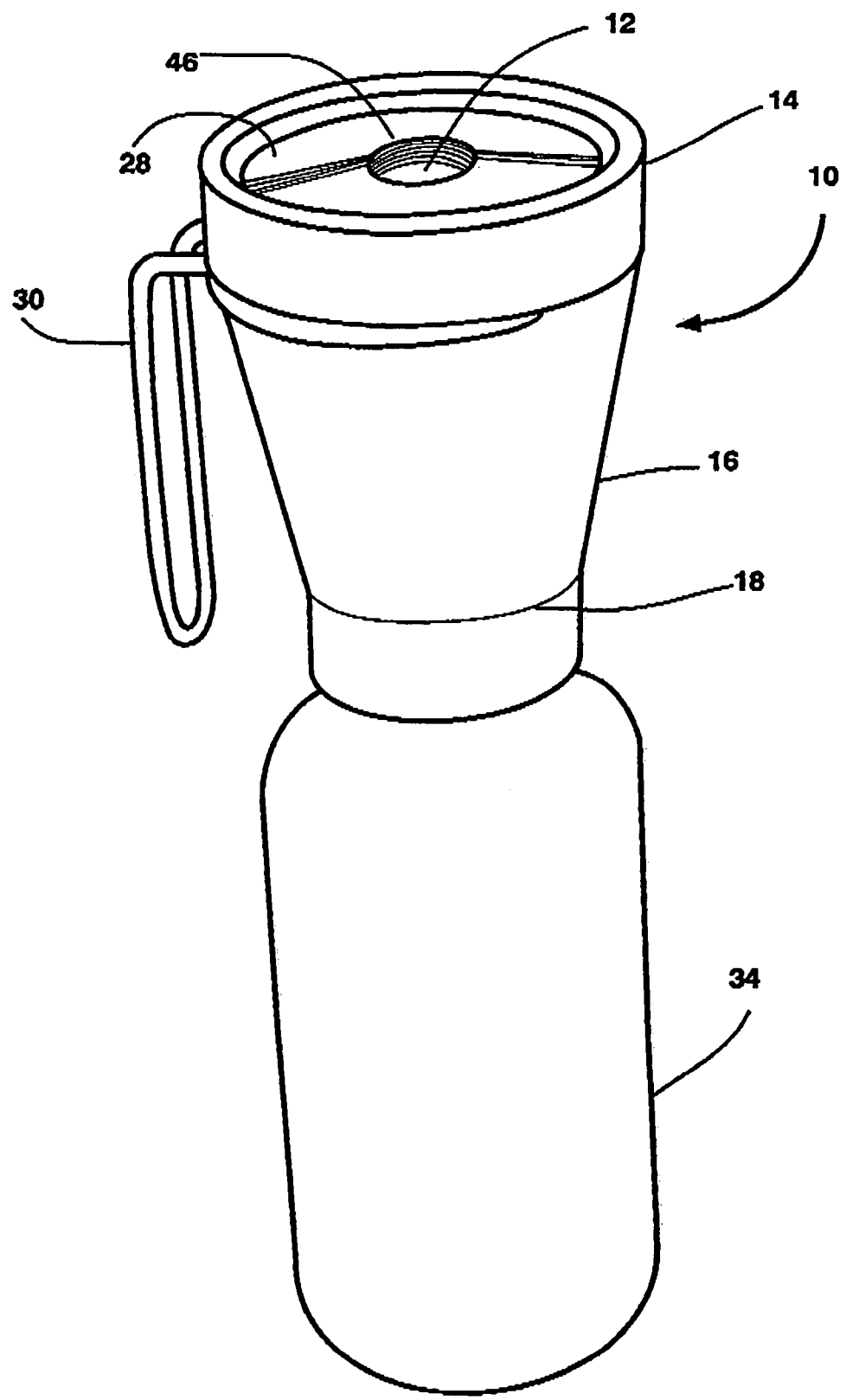
FIG. 1 is a perspective view of the present embodiment of the first preferred embodiment of the present invention.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

The present invention is a method and device for applying germicidal solutions called teat dips to cattle teats. The method of the invention principally includes the steps of dipping a teat into a quantity of a solution so as to provide teat dip coverage up to a desired level; wiping this teat so as to remove the excess material from this teat; and recollecting the wiped material for re-use. This method is a significant improvement over the prior methods, which simply dip the teat and then let the excess teat dip fall off of the teat and be wasted, or that uses a spray applicator to spray material over the device. The method of the prior invention is best performed by a single device, which allows the dipping, wiping and recollecting steps to be performed in two simple motions, an upward movement to place the device upon the teat and a downward movement to remove the device from the teat. The present invention further comprises additional steps that may be utilized and are more easily described in view of the preferred present embodiment of the device of the present invention.

FIGS. 1-4 show various views of the preferred present invention of the embodiment of the device of the invention. While the preferred embodiment of the present invention is the only embodiment of the device of the invention that is shown, it is to be distinctly understood that the invention is not limited thereto but may be variously configured and embodied according to the necessities of the user of the present invention. Referring first to FIG. 1, a perspective assembled view of the device of the preferred first embodiment of the present invention is shown. This device is a germicidal application device 10 made up of a cleansing chamber 12 defined by a body 16 with an open first end 14 and extending to a closed second end 18. A circumvolving inner ring 20 (shown in FIG. 3) is positioned within the teat-cleaning device and is configured to allow passage of an animal teat, typically a bovine teat, into the chamber defined within the body 16. A wiping device 28 is positioned near the open first end 14 of the cleaning device and is configured to allow passage of a teat through the apertures 46, 46' and into the chamber 12.

In the preferred embodiment of the invention, the cleaning chamber 12 is attached to a reservoir bottle 34. The second end of the chamber 18 has a portion configured for connection with a reservoir bottle 34. This reservoir bottle is, in the preferred embodiment, made of a compressible material whereby when the bottle is squeezed material is forced from the reservoir up through a transport conduit 22 (shown in FIG. 3) and into the chamber 12. For ease of use, a handle 30 is connected to the body 16 of the cleaning attachment.

In use, the device is utilized by providing a preselected quantity of a desired type of teat dip into the container 12. The entire cleansing attachment is then placed beneath a cow's udder and raised so that the teat enters through the aperture 46 within the wiping device and is dipped into the germicidal solution so as to coat the entire teat. Once the teat has been appropriately wetted, the device is then lowered so as to remove the teat from within the unit. As the device 10 is lowered, the wiping device 28 contacts the teat and wipes the teat dip so that adequate coverage of the teat is obtained and that all excess teat dip material is removed from the teat and recollected within the chamber 12.

Figure 2:
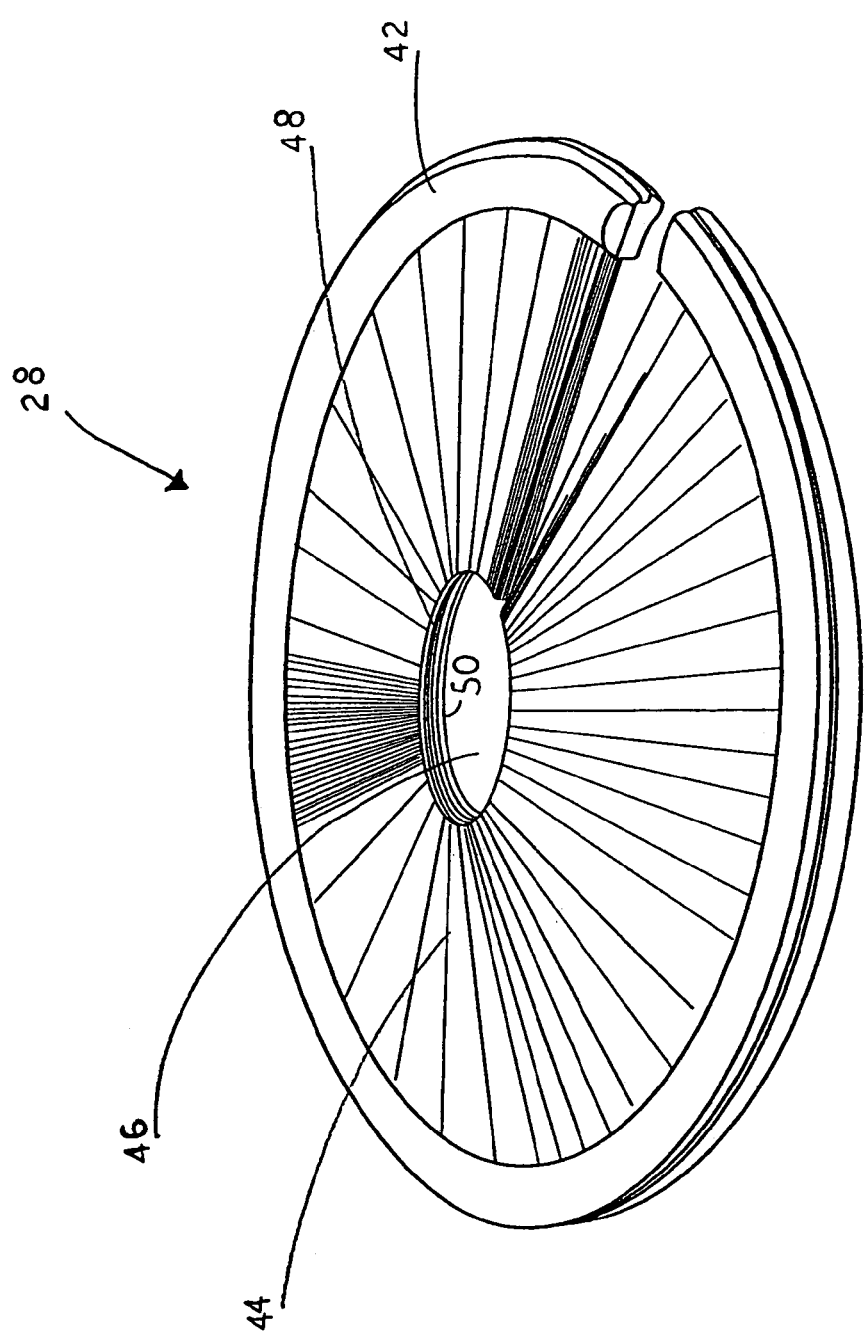
FIG. 2 is a perspective view of the preferred embodiment of the wiping device shown in FIG. 1.

Referring now to FIG. 2, a detailed view of the wiping device 28 of the preferred embodiment of the device portion of the present invention is shown. The wiping device 28 of the preferred embodiment is a generally circular brush having a plurality of soft bristles 44, connected to a split outer ring 42, in various layers 48, 50. These bristles 44 define an aperture 46, which is configured to have a diameter that is slightly smaller than the average diameter of a cattle teat. The wiping device 28 is configured to be positioned and held upon a generally circumvolving ring (shown in FIG. 3) by a clip. The split outer ring 42 allows for increased flexibility of the bristles 44 and provides greater wiping capacity to the bristles 44. While the generally circular brush with the split ring and the layers of bristles is shown in the preferred embodiment, it is to be distinctly understood that the invention is not limited thereto but may be variously embodied according to the needs and necessities of the user, therefore the description of the preferred embodiment is not limited thereto but may be variously embodied according to the necessities of the user.

Figure 3:
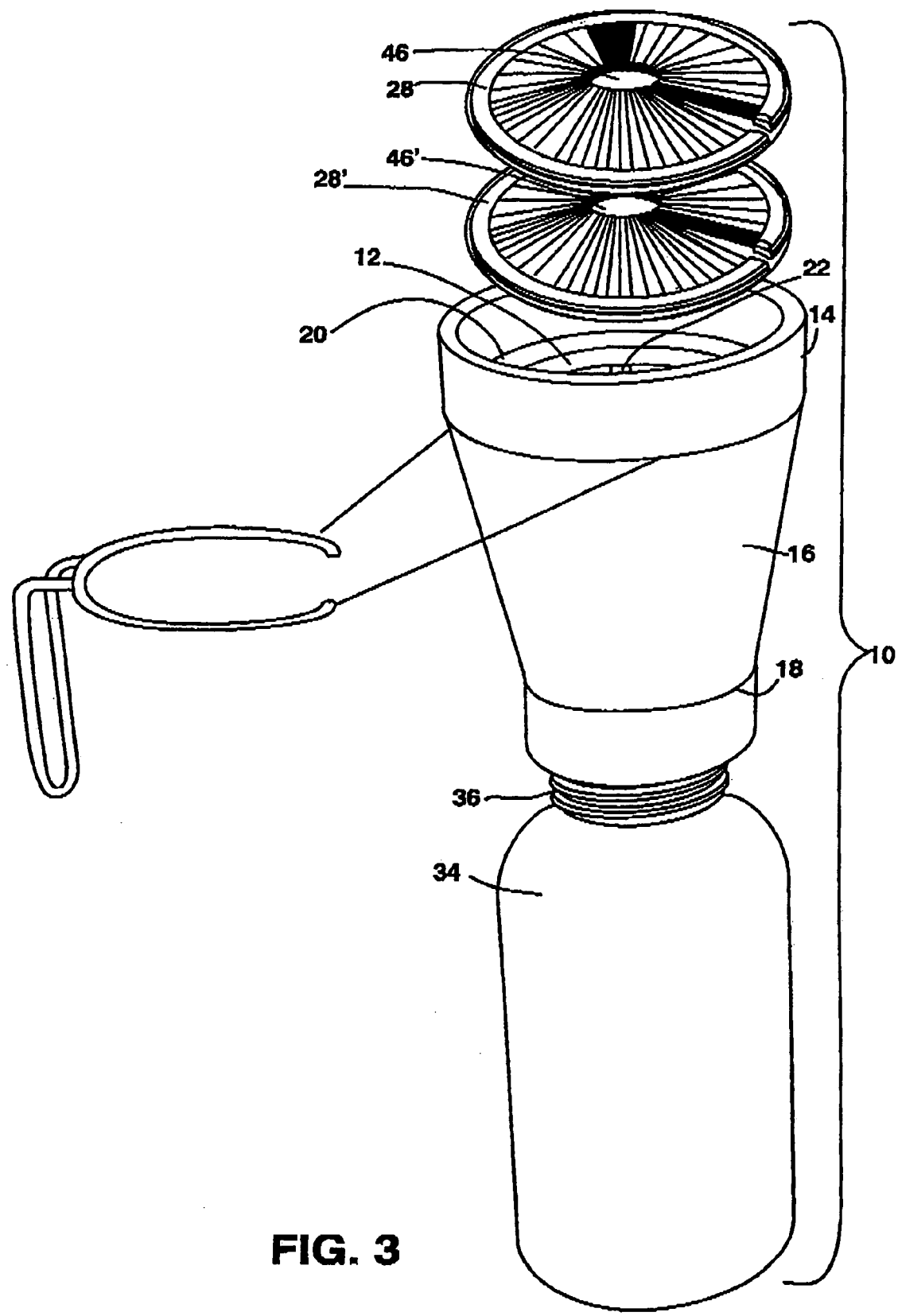
FIG. 3 is a perspective exploded assembly view of the embodiment shown in FIG. 1.
Figure 4:
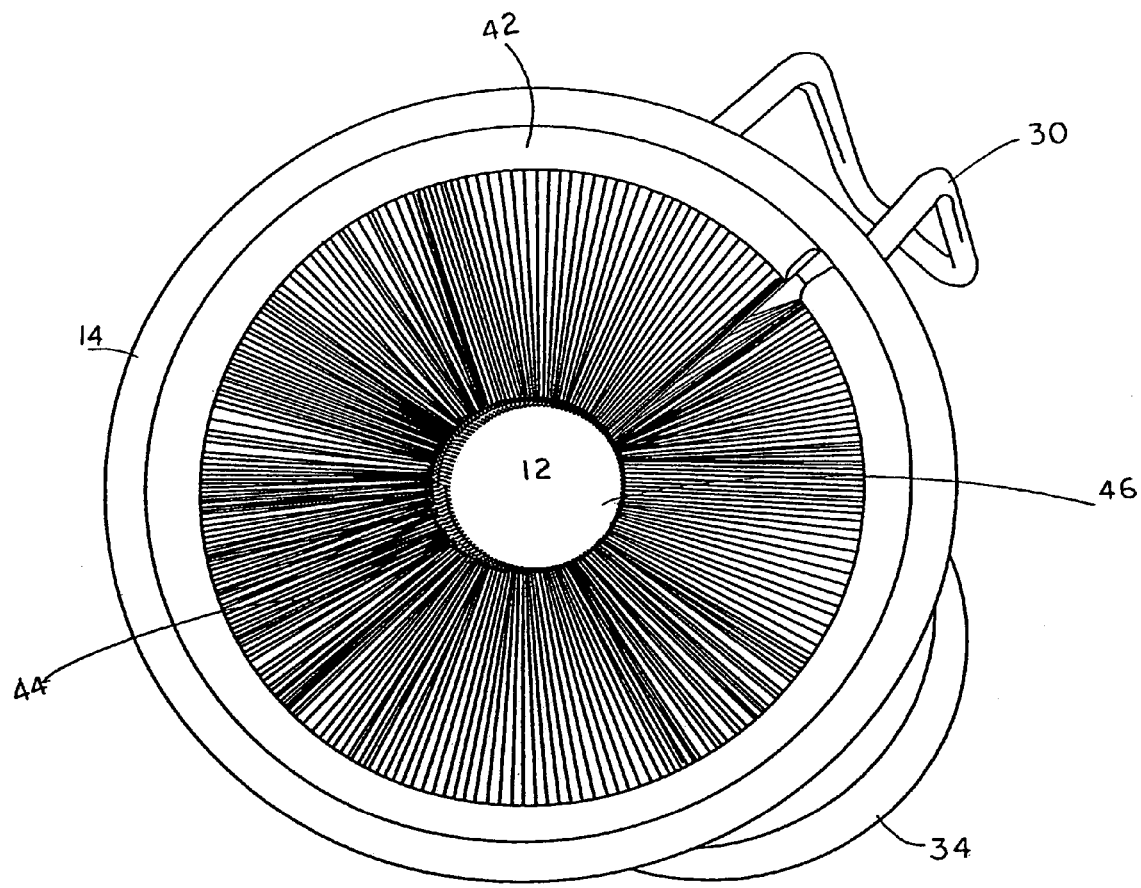
FIG. 4 is a top view of the embodiment shown in FIG. 1.

Referring now to FIG. 3, an exploded view of the present invention is shown. FIG. 3 shows that the transport conduit 22, which brings solution from the reservoir container 34, is positioned to terminate within a circumvolving ring 20 wherein the wiping device 28 is connected. Thus, when the transport conduit 22, which has a first end positioned within the reservoir bottle 34 and a second end 26 that terminates at or near the circumvolving ring 20. This configuration allows the wiping device to be wetted with the new solution as it is transported from the reservoir container 34 and is moved into the cleaning chamber 12. While this configuration is shown in the preferred embodiment, it is to be distinctly understood that the invention is not limited thereto but may be variously embodied to include all of the designated features of the present invention.

The wiping device 28, which in the preferred embodiment is a generally circular brush defining a round aperture, is positioned above the circumvolving ring and assists to wipe a teat as it enters and exits the cleansing attachment 12. In the preferred embodiment, a second wiping device 28' is positioned beneath the circumvolving ring 20 thus providing two wiping devices. In the preferred embodiment, the various layers 48, 50 of the brush provide this wiping assistance.

The reservoir container 34 is made up of a compressible material so that it can be manually squeezed so as to force liquid to travel up the transport conduit through the open first end of the conduit and wet the wiping devices 28, 28'. Thus, as a germicidal liquid is removed from the cleansing chamber 12, it is replaced by liquid from the reservoir container that is pushed into the cleaning chamber 12 through the transport conduit 22. In the preferred embodiment, the cleansing chamber 12 together with the wiping device is an attachment that is configured to attach to the top 36 of the reservoir container. However, it is to be understood that the invention may be variously embodied to include various features, and that it may be alternatively embodied to attach to other types of devices as well, including embodiments wherein the transport conduit provides delivery of germicidal solution from a storage tank positioned in a distant location.

In use, the present invention is utilized by the following process. First, a desired amount of germicidal liquid is placed within the cleansing chamber 12. In the preferred embodiment, this is accomplished by squeezing the reservoir container until the desired amount of liquid has been pushed through the conduit 22 and into the chamber 12. Once this has been accomplished, the device 10 is raised so that the teat passes through the wiping devices 28, and into the cleansing attachment 12. This device 10 is continually raised until the teat has been sufficiently coated with germicidal solution so as to provide the positioning of liquid in the desired positions. Once this desired level has been arrived at, the device 10 is removed from its position upon the teat. As the device is lowered, the wiping device 28 contacts the teat and wipes the excess material from the teat and recollects this solution within the chamber 12. In the event that additional material needs to be added to the cleaning chamber, this can be added by simply compressing the bottle and forcing the liquid into the cleaning chamber.

The method and device of the present invention significantly reduces the amount of material that is wasted by dripping or otherwise falling off of the teat and provides significant cost savings to a user. This device, while simple, provides substantial monetary and environmental savings. For example, a 1,000-cow dairy farm milking their cows three times a day uses approximately 400 gallons of germicide a month. That is six dollars per gallon and results in about $2,400 per month. This new device enables such a location to eliminate seventy-five percent of the usage or 300 gallons per month for a total savings of $1,800 per month. Also saving 300 gallons per month of germicides from being spread upon the earth as waste. The reservoir bottles 34 themselves can be filled in conventional manners from dispensing mechanisms that are well known in the art.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

I claim:

1. A method for applying germicidal non-foaming teat dip solution to a teat comprising the steps of:

providing a reservoir container, having a top and an outer surface and defining a reservoir capable of holding a pre-selected quantity of a desired germicidal substance therein; an attachment connected with said top portion of said reservoir container, said attachment having a open first end configured to receive a teat therein, and extending along a body to a closed second end, said closed second end connected with said top portion of said reservoir container whereby material may pass from said reservoir container into said attachment through a transport conduit; said transport conduit is positioned within said attachment and having a first end and a second end and defining a passageway that extends from said first end to said second end along a length, said length sufficient so as to transport germicidal material from said reservoir to a desired location within said attachment and proximate said attachment open first end; and at least one wiping device fixedly laterally positioned within said attachment; said wiping device comprised of a generally circular brush having pluralities of soft bristles connected to an outer ring in layers, said outer ring configured to fit within said open first end of said attachment, said attachment further comprises a circumvolving ring positioned with said attachment, said ring configured for connection with at least one of said wiping devices, said wiping device configured to be wetted by said solution to apply said solution to said teat by wiping;

inserting said teat within said attachment first end;

applying a quantity of said solution to said teat as said teat is inserted into said attachment first end, said application done by said wiping device;

withdrawing said body part from said attachment first end;

wiping said teat utilizing said wiping device as said teat is withdrawn from said attachment first end; and recollecting excess germicidal non-foaming teat dip solution that is removed from said teat when said teat is wiped by said wiping device.

* * * * *